US 6,709,379 B1

(12) United States Patent
Brandau et al.

(10) Patent No.: US 6,709,379 B1
(45) Date of Patent: Mar. 23, 2004

(54) IMPLANT WITH CAVITIES CONTAINING THERAPEUTIC AGENTS

(75) Inventors: Wolfgang Brandau, Muenster (DE); Alfons Fischer, Essen (DE); Thomas Sawitowski, Essen (DE); Güenter Schmid, Velbert (DE)

(73) Assignee: Alcove Surfaces GmbH (DE)

( * ) Notice: Subject to any disclaimer, the term of this patent is extended or adjusted under 35 U.S.C. 154(b) by 0 days.

(21) Appl. No.: 09/830,895

(22) PCT Filed: Nov. 2, 1999

(86) PCT No.: PCT/EP99/08346

§ 371 (c)(1),
(2), (4) Date: May 2, 2001

(87) PCT Pub. No.: WO00/25841

PCT Pub. Date: May 11, 2000

(30) Foreign Application Priority Data

| Nov. 2, 1998 | (DE) | 198 50 352 |
| Dec. 1, 1998 | (DE) | 198 55 421 |
| Feb. 18, 1999 | (DE) | 198 07 006 |
| Mar. 9, 1999 | (DE) | 198 10 188 |

(51) Int. Cl.$^7$ ............................................. A61N 5/00
(52) U.S. Cl. ...................... 600/3; 600/7; 604/891.1; 623/1.39; 623/1.42; 623/1.45
(58) Field of Search ........................ 600/2–3, 7–8; 604/891.1, 892.1, 890.1; 623/1.39, 1.42–1.43, 1.45–1.46, 1.49

(56) References Cited

U.S. PATENT DOCUMENTS

| 3,952,334 A | * | 4/1976 | Bokros et al. ............. 427/2.25 |
| 3,987,219 A | * | 10/1976 | Arvidsson ................... 427/297 |
| 4,323,055 A |   | 4/1982 | Kubiatowicz |
| 4,818,572 A |   | 4/1989 | Shimamune et al. |
| 5,464,438 A | * | 11/1995 | Menaker ..................... 623/1.43 |
| 5,478,237 A |   | 12/1995 | Ishizawa |
| 5,716,400 A | * | 2/1998 | Davidson .................... 623/2.42 |
| 5,769,883 A |   | 6/1998 | Buscemi et al. |
| 5,843,172 A | * | 12/1998 | Yan ............................ 604/104 |
| 6,206,915 B1 | * | 3/2001 | Fagan et al. ................ 623/1.15 |
| 6,210,436 B1 | * | 4/2001 | Weadock .................... 623/1.39 |
| 6,240,616 B1 | * | 6/2001 | Yan ............................ 29/527.2 |
| 6,253,443 B1 | * | 7/2001 | Johnson ....................... 29/557 |
| 6,273,908 B1 | * | 8/2001 | Ndondo-Lay ............... 606/194 |
| 6,287,628 B1 | * | 9/2001 | Hossainy et al. ............ 427/2.3 |
| 6,322,588 B1 | * | 11/2001 | Ogle et al. .................. 623/1.46 |
| 6,322,819 B1 | * | 11/2001 | Burnside et al. ............ 623/1.15 |
| 6,379,381 B1 | * | 4/2002 | Hossainy et al. .............. 441/1 |
| 6,506,437 B1 | * | 1/2003 | Harish et al. .............. 427/2.25 |

FOREIGN PATENT DOCUMENTS

| CA | 2235031 | 4/1998 |
| DE | 31 01 679 A1 | 12/1981 |
| DE | 31 01 679 | 12/1981 |
| DE | 0 156 003 | 7/1982 |
| DE | 32 41 589 A1 | 5/1984 |
| DE | 32 41 589 | 5/1984 |
| DE | 31 01 679 C2 | 9/1989 |

(List continued on next page.)

OTHER PUBLICATIONS

European Patent Office, Patent Abstracts of Japan, Jul. 6, 1999, 11–181596, Inventor: Yamada Kunihiro.

(List continued on next page.)

Primary Examiner—Henry Bennett
Assistant Examiner—Amanda Flynn
(74) Attorney, Agent, or Firm—Nixon Peabody LLP; Stuart J. Friedman

(57) ABSTRACT

The invention relates to an implant and a method for the production of an implant. The implant has a covering layer that is preferably made of aluminium oxide and provided with uniform cavities and separate openings on the surface side of the covering layer in order to receive a therapeutic agent which can be released according to requirements when the implant is in place.

48 Claims, 7 Drawing Sheets

FOREIGN PATENT DOCUMENTS

| | | |
|---|---|---|
| DE | 40 40 850 A1 | 6/1992 |
| DE | 40 40 850 | 6/1992 |
| DE | 41 08 772 | 9/1992 |
| DE | 41 08 772 A1 | 9/1992 |
| DE | 43 11 772 | 10/1993 |
| DE | 43 11 772 A1 | 10/1993 |
| DE | 296 07 916 | 8/1996 |
| DE | 296 07 916 U1 | 8/1996 |
| DE | 195 37 872 | 4/1997 |
| DE | 195 37 872 A1 | 4/1997 |
| DE | 297 01 758 | 5/1997 |
| DE | 297 01 758 U1 | 5/1997 |
| DE | 297 02 671 U1 | 5/1997 |
| DE | 297 02 671 | 5/1997 |
| DE | 297 08 689 U1 | 8/1997 |
| DE | 297 08 689 | 8/1997 |
| DE | 297 08 803 U1 | 9/1997 |
| DE | 297 08 803 | 9/1997 |
| DE | 297 08 879 | 9/1997 |
| DE | 297 08 879 U1 | 9/1997 |
| EP | 0 433 011 A1 | 6/1991 |
| EP | 0 433 011 B1 | 6/1991 |
| EP | 0 210 269 B1 | 10/1991 |
| EP | 0 520 721 A2 | 12/1992 |
| EP | 0 593 136 B1 | 4/1994 |
| EP | 0 593 136 A1 | 4/1994 |
| EP | 0 608 997 A1 | 8/1994 |
| EP | 0 853 957 A3 | 7/1998 |
| EP | 0 853 957 A2 | 7/1998 |
| EP | 0 875 218 A2 | 11/1998 |
| WO | WO 86/04248 | 7/1986 |
| WO | WO 90/14801 | 12/1990 |
| WO | WO 98/48851 | 11/1998 |

OTHER PUBLICATIONS

Dunn et al., "Anodized Layers on Titanium and Titanium Alloy Orthopedic Matereials for Antimicrobial Activity Applications", 1992, pp. 123–137, Materials & Manufacturing Processes, 7(1).

Hornyak et al., "Gold Clusters and Colloids in Alumina Nanotubes", Dec. 1997, pp. 1951–1956, Chemistry: A European Journal, vol. 3, No. 12.

Hanaoka et al., "Three–Dimensional Assemblies of Gold Colloids in Nanoporous Alumina Membranes", 1998, pp. 807–812, European Journal Inorg. Chem.

Hanaoka et al., "Alumina Membranes—Templates for Novel Nanocomposites", 1998, pp. 367–373, Applied Organometallic Chemistry, vol. 12.

Schultze et al., "Regular Nanostructured Systems Formed Electrochemically: Deposition of Electroactive Polybithiophene into Porous Silicon", 1995, pp. 1369–1383, Electrochimica Acta., vol. 40, No. 10.

Tsujii et al., "SuperolabstoBende Oberflachen", 1997, pp. 1042–1044, Angew. Chem. 109, Nr. 9.

Shibuichi et al., "Super Water–and Oil–Repellent Surfaces Resulting from Fractal Structure", 1998, pp. 287–294, Journal of Colloid and Interface Science 208, Article No. C5985813.

Berressem, "The Birth of New Delivery Systems", Feb. 1999, pp. 29–32, Chemistry in Britain.

* cited by examiner

IMPLANT WITH CAVITIES CONTAINING THERAPEUTIC AGENTS

FIELD OF THE INVENTION

The present invention relates to an implant and to a method for producing an implant and, more particularly, to implants having cavities for absorbing therapeutic agents.

BACKGROUND OF THE INVENTION

Here, the term "implant" is first of all, to be understood in a narrow sense, as referring to an element, at least temporarily insertable into the body of an animal or human, which may perform, e.g., therapeutic, support and/or joint functions, like temporary implants, for example the so-called "seeds", or stents for tumor treatment or therapy, tracheal stents and the like. However, in a broader sense, this term is also be understood as referring to elements or the like being able to be brought, preferably temporarily, into contact with the body on the outside.

Implants in the form of stents are applied, e.g., for supporting widened vessels. After having widened constricted vessels, these tube-shaped inserts are inserted and then radially widened so that the stents support the vessel walls from the inside.

The stents grow into the vessel walls within about one to three months. A local radioactive irradiation of the vessel walls has proved to be effective in preventing an overgrowth of the vessel walls towards the inside which may lead to a re-stenosis, i.e. a re-constriction. The following possibilities present themselves in this respect.

Firstly, a balloon catheter filled with a radioactive liquid is applied. Since the balloon catheter at least partly closes the vessel in its expanded condition, contact with the vessel wall and thus application of the balloon catheter is very strongly limited in time. In order to locally obtain an effective dose, very large activity amounts must thus be applied which leads to technical problems in protection against radiation. In addition, there is a very high risk for the patient in the event of a mechanical failure of the balloon.

Secondly, a sealed radiation source may be inserted via a catheter. Here, because of the limited dwell time of the catheter in the vessel, great amounts of activity must also be applied which demands a great technological effort with regard to protection against radiation. Furthermore, there is the problem of centering the radiation sources.

Thirdly, radioactive stents may be applied. As a result, the aforementioned problems and risks are avoided and the desired or effective dose may be achieved with low amounts of radioactivity over an extended exposure time.

In the last case, i.e. the radioactive embodiment of the stents, it is already known to provide ion implantation. Here, radioactive phosphorus ($^{32}$P) is implanted in existing stent surfaces by means of an ion beam. Further, it is known that a nickel-titanium stent may be bombarded with protons in a cyclotron or the like, in order to activate the titanium contained in ordinary nickel/titanium alloys into radioactive vanadium ($^{48}$V).

Both ion implantation and proton activation are marked by a great technological effort, i.e. the stents can only be produced on a "custom-made basis". Moreover, both methods are hitherto limited to a few manufacturing sites and a few radionuclides.

A further method for producing radioactive stents is provided by electrochemically precipitating radioactive rhenium on stent surfaces and then by covering them with a gold a layer as a protective layer. Here, as in all multi-layer structures, there is the risk of segmentation, i.e. detachment, which is very high for stents because of the deformation during the radial widening on the inside of the vessels. Even if only the protection layer is dissolved or in the event that it was applied incompletely, there is the risk that radioactive rhenium lying freely on a large surface area may then be partly dissolved in the blood and may be transported to other locations in the body with undesirable consequences.

Moreover, having drugs act as locally as possible may be meaningful in order to prevent, e.g., an expulsion of the implant or to perform local tumor treatment, for example.

A stent is already known from CA-A-2,235,031 corresponding to EP-A-0 875 218 which forms the starting point of the present invention; a stent which comprises a non-porous support with a porous covering layer in one embodiment. The porous covering layer is formed of sintered metal particles. A drug or a therapeutic agent is absorbed in the pores of the porous covering layer and it may be re-released from the stent in the implanted state if the porous covering layer is covered with a dissolvable or permeable covering layer for example. A radioactive material may also possibly be applied as a drug.

In the known stent, it is detrimental that the sintered metal particles of the porous covering layer form very irregular, indefinite pores. Accordingly, in the case of a drug to be released, only a relatively indefinite release behavior is achieved.

When a radioactive material is absorbed in the pores of the covering layer, there is the risk that the radioactive material uncontrollably and undesirably escapes because of irregular pores with indefinite openings. The optionally provided coating of the covering layer does not provide sufficient protection in this respect.

The mechanical strength and rigidity of the covering layer formed from the combined sintered metal particles is not very good, especially when deforming the stent. In particular, there is the risk that at least some individual metal particles break away from the covering layer. In addition, there is the risk of segmentation of the covering layer, especially in the radial widening of the stent. Here, there is the risk that, for example, blood circulation will transport portions of the covering layer to other locations in the body with undesirable consequences. This risk is particularly high in the application of radioactive material which, as a drug or a therapeutic agent, should remain fixed in the porous covering layer.

In addition, nickel, in particular, is suspected in metal implants of at least favouring excess cell growth, in particular in the area around an inserted implant. Moreover, other metals from metal surfaces—even when only in small amounts—which may also be dissolved by body fluids, such as blood, are increasingly made responsible for undesirable consequences or at least unpredictable reactions in the body. In this respect, the large surface area of the metal particles from the known stent's porous covering layer which may come into contact with body fluids or with the body tissue growing into the porous covering layer, is particularly detrimental. However, e.g., the application of ceramic covering layers or the coating of metal surfaces for use with implants is already known, for example from DE-A-43 11 772, DE-A 40 40 850, DE-A-32 41 589 or EP-A-0 520 721.

SUMMARY OF THE INVENTION

The object of the present invention is to provide an implant and a method for producing an implant so that an implant, in particular formed as a stent, may be produced relatively simply, wherein in particular the aforementioned drawbacks of the prior art may be avoided or at least minimized and wherein a therapeutic agent may be absorbed by the implant and—if desired—is locally re-releasable in the implanted condition, and in particular so that the implant, in particular a stent, enables radionuclides to be fixed securely on or in the surface.

In particular, the covering layer comprises a plurality of defined cavities with separate openings to the surface of the covering layer for absorbing at least one therapeutic agent. The term "cavities" should also be understood here as defined vacancies in crystal structures or the like which are suitable for absorbing a therapeutic agent.

Unlike the prior art, the structure of defined and preferably separate cavities in the covering layer allows very precise amounts of a therapeutic agent to be stored in the cavities, to be fixed in the cavities if necessary and to be re-released—if desired—in the implanted condition under definite conditions, such as with a desired release rate.

The term "therapeutic agent" should be understood in accordance with the present invention as drugs in the broadest sense, optionally also radioactive material or other therapeutic substances. In particular, all therapeutic agents, which in EP-A-0 875 218 are designated as "medication" or receptor-agonists, receptor-antagonist, enzyme inhibitors, neurotransmitters, cytostatitics, antibiotics, hormones, vitamins, metabolic substrates, anti-metabolites, diuretics, and the like are also considered to be therapeutic agents in accordance with the present invention.

In addition, an implant as proposed is provided with a support and a covering layer, wherein preferably the covering layer at least essentially consists of a metal oxide and/or ceramic material. In particular, the covering layer essentially comprises aluminum oxide, magnesium oxide tantalum oxide, iron oxide and/or titanium oxide. Such a covering layer is relatively easy to produce, for example via electrolytic precipitation and oxidization, and it forms a highly chemically and mechanically stable, in particular, very dense coating of the support. This coating may prevent, at least to a large extent, (ionic) dissolution of nickel or other metals from the support. Excess cell growth induced by the dissolved metals may thus at least be minimized in the surroundings and in the contact area of the implant respectively.

A simple structure of the cavities in the covering layer is preferably achieved by anodic oxidization of a surface layer which may be part of the support or of a coating deposited thereon.

Similarly-shaped cavities of defined dimensions may thus be formed in a simple way. Preferably, highly similarly-shaped cavities may be produced very simply by electrolytically forming an aluminium oxide layer as a covering layer on the surface of the support. In such an artificial oxidization of aluminium (anodization), defined cavities may be formed in dependence with the applied voltage. Apart from aluminium oxide, all the so-called valve metal oxides, e.g. titanium and tungsten oxides, are particularly suited for this purpose. Furthermore, magnesium oxide is also useful.

By varying the electrical voltage during the anodization, the diameter of the cavities and the surface density of the cavities, i.e., the number of cavities per unit surface, may be varied. The length of the cavities depends on the duration of the anodization. As a result, the shape of the cavities may be controlled in large ranges, so that e.g. in view of a desired release behavior (release rate, release amount), an optimized shape of the cavities may be produced in a simple way. For example, the cavities are formed at least essentially as tubes and extend from the surface of the covering layer, essentially perpendicularly into the inside of the covering layer, wherein the portion of the cavities and/or their openings are reduced in diameter or proportionally in area in order to obtain desired properties.

When needed and depending on the application, several therapeutic agents which, for example, are re-released in succession and/or with an irregular release rate in the implanted state, may be absorbed by the cavities. For example, therapeutic agents of different molecular size may thus be absorbed in different cavities of suitable dimensions of the covering layer of the implant. If necessary, the cavities or their openings to the surface of the covering layer, may also be formed small as compared with the components normally contained in body fluids, like blood, in particular proteins, with the result that an otherwise occurring dissolution or wash-out of the therapeutic agent situated in the cavities does not occur through blood macro-molecular components or the like, as the latter cannot penetrate into the cavities.

The integration of the cavities in the covering layer of the support makes a relatively thin structure possible with a correspondingly low tendency to segmentation, i.e. a structure with favorable mechanical properties.

The forming of cavities in certain locations with a relatively low superficial extent with respect to the superficial extent of the covering layer leads to the advantage that the mechanical properties of the covering layer essentially only depend on the material of the covering layer and not on the therapeutic agent or the like in the cavities. Accordingly, an optimized covering layer with regards to the large mechanical stress in stents can be applied on the one hand and on the other hand optimally suitable therapeutic agents with regards to the treatment can be used.

Basically, the cavities may be linked with one another. But, preferably, the cavities are formed separated from one another, preferably with respect to low height or thickness of the covering layer.

In particular, in the case of separately formed cavities, it is possible to arrange a therapeutic agent or several therapeutic agents in the cavities in a different concentration or amount or with different release behavior in order to achieve, for example, a desired inhomogeneous dose distribution in time and/or in space, with, e.g., a higher dose at the ends of a stent.

The introduction of the therapeutic agent and/or the complexing agents or binding partners in the cavities of the covering layer and by subsequent addition of the therapeutic agent or the complexing agents or binding partners, so that it (they) is (are) absorbed by the cavities or sucked into them. If necessary, this is repeated, e.g., for cavities in certain surface areas, in particular end areas of the implant, in order to achieve a local increase in the amount of absorbed therapeutic agent.

Alternatively or additionally, introduction of the therapeutic agent or of the binding partners in the cavities may be achieved or assisted by means of ultrasound which may purge air or other gases present in the cavities upon dipping the implant into the agent to be introduced.

A further aspect of the present invention consists in fixing or binding the therapeutic agent or the therapeutic agents in the cavities according to needs, for example ionically via hydrogen bridges, via complexing agents, via Van der Waal forces, or the like in order to achieve the desired release or liberation of the therapeutic agent or of the therapeutic agents. Bonds are also possible which are chemically or enzymatically cleaved or broken up in biological systems and thereby cause a release. Desired properties of the cavities may be obtained relatively easily by chemically altering the walls of the cavities, in particular by chemically fixing suitable binding partners for the relevant therapeutic agent on the wall surfaces.

Finally, it should be pointed out that the implant as proposed may also be provided with cavities open to the outside in the covering layer, wherein the size of the cavities may be selected so that cells or portions of cells from the body tissue adjacent to the implant may grow into the cavities and thus, for example, a very secure anchoring of the implant in the body may be achieved.

In addition, there is the possibility of covering the covering layer or the openings of the cavities with a cover layer as protective layer. This cover layer may be made very thin, as essentially it is only used for obtaining the desired surface properties or a covering up of the material of the covering layer. For example, depending on the application, the cover layer may be formed so that it dissolves or loosens from the surface of the covering layer in the body, for example due to the body's temperature, to artificial heating, chemical or enzymatic effects from liquids or body-specific substances, or so that it is permeable for a therapeutic agent to be absorbed in the cavities. In particular, the cover layer may be formed like the one in the coating of porous material disclosed in EP-A-0 875 218.

In the specially provided application of radioactive material as therapeutic agent, an essential aspect of the present invention is that the radioactive material is not localized or arranged over the entire surface, but only in individual locations and in the covering layer of a support, respectively. The covering layer may basically be formed by a surface layer, i.e. an upper portion, of the support or in particular by a layer or coating applied on the surface of the support. Thus, it is possible to form the cavities or their openings to the surface of the covering layer, small as compared with the components normally found in blood, particularly proteins, so that in the case of exposure to radioactive material over a large area, no normally occurring dissolution or removal of the radioactive material by macromolecular blood components occurs, as the latter cannot penetrate into the cavities.

A further advantage provided by the cavities lies in that the walls of the cavities create a very large inside surface area. This internal surface represents an essentially larger surface than the outside surface of the covering layer and accordingly it allows a particularly tighter or stronger binding of more radioactive material as compared with standard multi-layer structures.

Another advantage provided by the arrangement of the radioactive material in the cavities lies in the different concentration of radioactive material according to need in order to achieve a desired spatial inhomogeneous dose distribution with, for example, a higher dose at the ends of a stent, by "filling" the cavities with different amounts of radioactive material in some areas of the surface.

Preferably, the cavities are formed at least essentially as tubes and extend from the surface of the covering layer, essentially perpendicularly into the inside of the covering layer, wherein the cross-sections of the cavities and/or their openings are preferably dimensioned so small that at least most of the proteins normally present in blood cannot penetrate into the cavities because of their molecular size, especially when they are only partly filled. Accordingly, the radioactive material provided in the cavities cannot be carried away by blood.

The use of an oxide layer, in particular of aluminium oxide, as a covering layer results in the additional advantage that the oxide layer in a liquid is subject to a sort of swelling which results in closure or further reduction of the opening area of the openings of the cavities in the covering layer, thereby providing an obstacle or impediment to the penetration of the relatively large proteins in blood. Of course, this swelling should be taken into account, when for example in a desired release of some therapeutic agents, the openings should not be closed.

Preferably, the introduction of the radioactive material and/or of the complexing agents in the cavities may be achieved by evacuating the cavities and then adding the radioactive material or the complexing agents which are then absorbed by the cavities or sucked into them, so to speak. When needed, this may be repeated e.g. for cavities in certain areas of the surface, in particular the end areas of the implant in order to achieve a local increase in radioactivity.

A further, independent aspect of the present invention lies in that the radioactive material, i.e., a particularly predetermined amount of a radionuclide or of different radionuclides, is to be fixed preferably in the cavities via complexing agents, such as amines, phosphines, carboxylates, and/or thiols. In particular, thiols are provided as complexing agents and for example, technetium and rhenium as radioactive material, since technetium(V) and rhenium(V)-compounds form metal complexes with sulphur-containing ligands which exhibit an extremely high stability in vivo. On the other hand, as another example, it is better to bind radioactive copper via carboxylates. With the help of complexing agents, in particular radioactive cations (metals) may thus be very tightly bound chemically, in particular in the cavities or pores of the covering layer. Preferably the complexing agents themselves are fixed or formed on the walls of the cavities, in particular by silanization, so that the complex is entirely fixed on the surface or in the covering layer of the support.

Alternatively, a binding of radioactive (non-metal) anions, for example iodine, may also be provided by forming a complex with appropriate complexing agents or with appropriate binding partners, for example in metals fixed in the cavities, such as noble metals, in particular silver.

A further, independent, essential aspect of the present invention lies in that different radionuclides with correspondingly different half-life times and emission energies, such as $^{186}$Re ($T_{1/2}$=90 hrs, $E_{\beta max}$=1.071 MeV) and $^{188}$Re ($T_{1/2}$=16.7 hrs, $E_{\beta max}$=2,116 MeV), are used together in predetermined amounts and ratios as a blend or mixture, respectively. An optimal dose distribution may thus be obtained for the relevant application both with respect to space and time considerations. The fixing of different radionuclides is especially enabled by the provision of cavities for absorbing the radionuclides, since the mechanical properties of the radionuclides or of the compounds formed with the radionuclides in the cavities play a minor role for the mechanical properties of the covering layer anyway because of the relatively small expansion of the cavities, so that radionuclides or radionuclide compounds which may not normally be used for large surface coatings may be absorbed in the cavities and fixed therein.

Moreover, there is the possibility of covering the covering layer or the openings of the cavities with a cover layer, for example in gold, as a protective layer. This cover layer may be made very thin as essentially it is only used for achieving the desired surface properties or a covering of the material of the covering layer, wherein, unlike the prior art, preventing contact between radioactive material and blood is of secondary importance, as the radioactive material is fixed in the cavities chemically and so it is already protected by the cavities anyhow. Furthermore, an essentially better adhesion of the cover layer on the covering layer may be achieved because of the free choice of materials, as essentially the mechanical and chemical properties of the covering layer are not influenced by the radioactive material used.

BRIEF DESCRIPTION OF THE DRAWINGS

In the following, the present invention will be explained in more detail with reference to the drawings of preferred embodiments. It shows.

Figure 1:
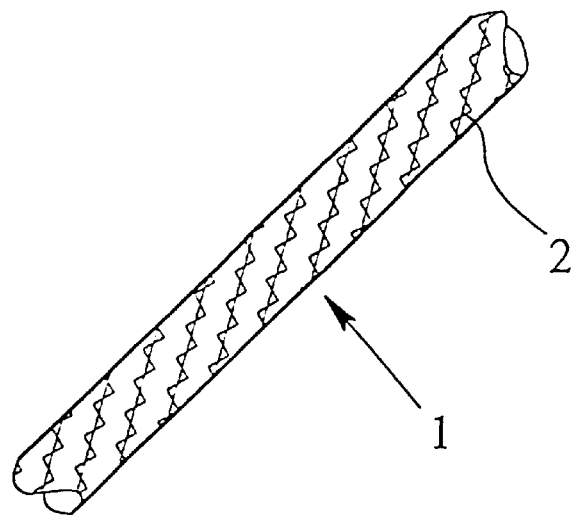
FIG. 1 a schematic illustration of a proposed implant formed as stent in the non-widened condition.
Figure 2:
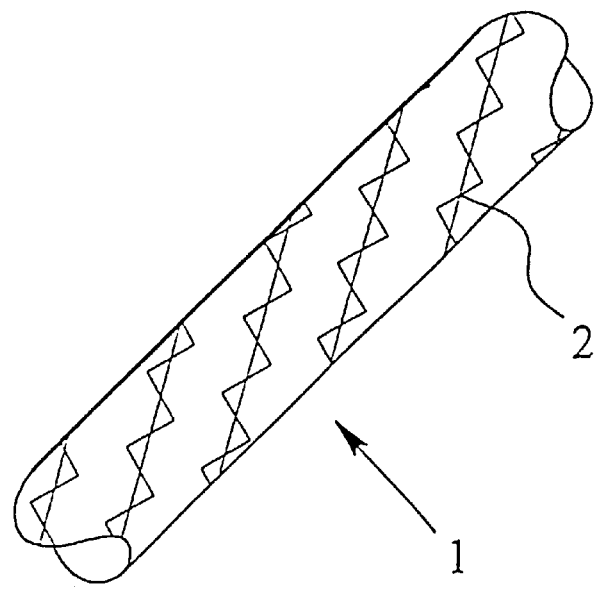
FIG. 2 a schematic illustration of the stent according to FIG. 1 in radially widened condition.
Figure 3:
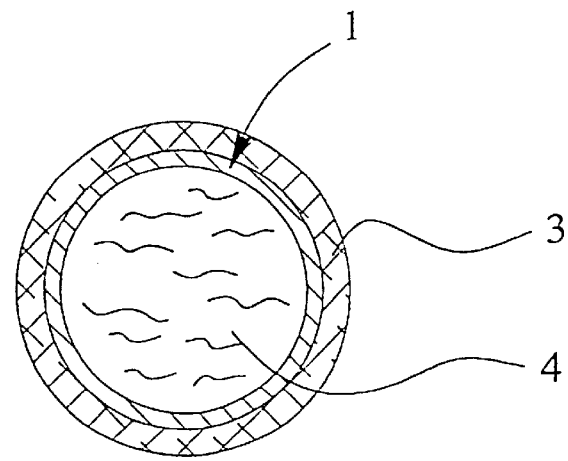
FIG. 3 a schematic cross-section of the stent inserted in a vessel and radially widened according to FIG. 2.

A proposed implant 1 is schematically shown in FIGS. 1–3. The implant 1 comprises the shape of a stent in the present exemplary embodiment, i.e. an essentially tube-shaped insert for vessels, as may be inferred from FIGS. 1 and 2.

The implant 1 or the stent comprises a preferably metal or metallized support 2. The support 2 is deformable here, so that the stent may be widened radially. FIG. 1 shows the stent in the non-widened state, FIG. 2 in the radially widened state.

FIG. 3 shows the stent in the radially widened state in a vessel 3, wherein the stent of the implant 1 sits close with its outer side on the inner side of the vessel wall and thus it supports the expanded vessel 3 from inside. The vessel 3 forms, therefore, body tissue which is in contact with the support 2. Furthermore, the support 2 or implant 1 is in contact with body fluids, like blood 4 which, e.g., flow through the vessel 3 and the stent.

Figure 4:
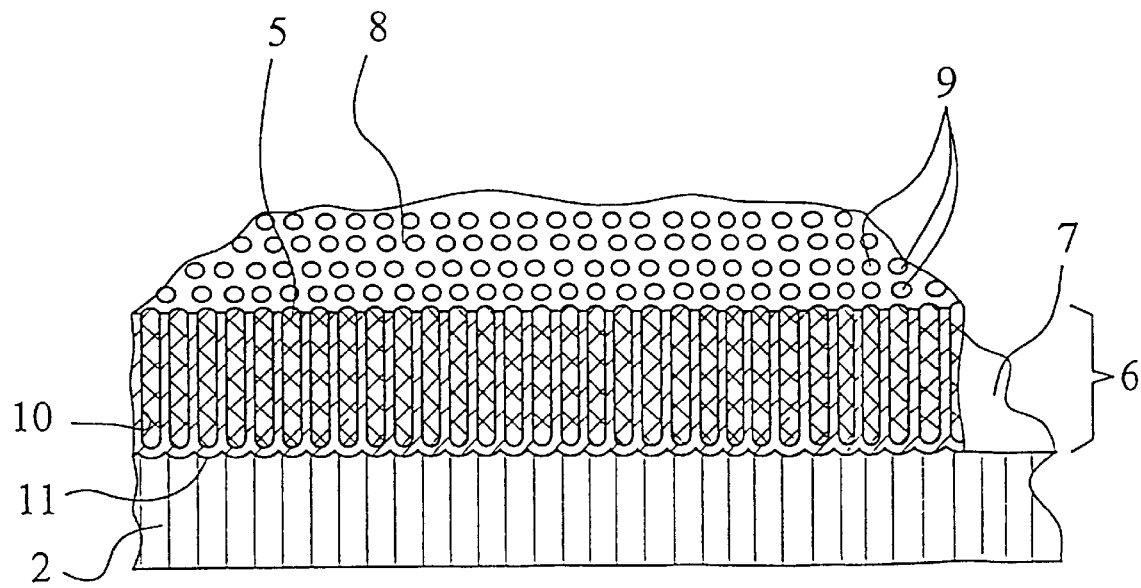
FIG. 4 a sectional enlargement of a support with an associated covering layer with several cavities of the implant.

At least one therapeutic agent or drug 5, respectively, is assigned to the support 2 which is fixed on or in the support 2 as inferred from the schematic partial enlargement of a surface area of the support 2 with an associated covering layer 6, partly cut away, according to FIG. 4. With regard to the therapeutic agent 5, reference is in particular made to the above definition.

Here, the covering layer 6 is applied preferably on the whole surface 7 of the support 2, for example by means of electrolytic precipitation and oxidization or a plasma deposition process. Alternatively, the covering layer 6 may, however, also be formed by a surface layer of the support 2, depending on the material of the support 2 and on the desired composition and structure of the covering layer 6.

The covering layer 6 comprises a plurality of distributed openings 9 spaced from one another and attached cavities 10 on its surface 8 facing away from the support 2. The therapeutic agent 5, which will be dealt with later on in more detail, is absorbed and optionally chemically fixed in the cavities 10, as will be explained later on in more detail with reference to FIG. 5a.

Here, the cavities 10 are formed essentially tube-like and each is closed on its ends. They extend from the surface 8 of the covering layer 6, essentially perpendicularly to the support 2.

In particular, the cavities 10 extend neither up to the surface 7 of support 2 nor into support 2, but they each terminate blind in the covering layer 6 and are separated from the surface 7 of the support 2 by a barrier layer 11 of the covering layer 6. The whole surface 7 of the support 2 is thereby at least extensively sealed off against body tissues and fluids. High chemical stability of the covering layer 6 in the body is of importance here.

Here, the cavities 10 are formed essentially as a circular cylinder. However, they may also comprise a polygonal cross-section or an irregular cross-sectional shape. Here, the cavities 10 extend essentially parallel to one another and are separated from each other without having the cavities 10 linked to one another. However, this is not absolutely necessary; possibly, links may also exist between the cavities 10 in the covering layer 6.

The covering layer 6 preferably comprises aluminium oxide which is precipitated or formed electrolytically on the surface 7 of the support 2. During electrolytic oxidization, the diameter of the openings 9 or of the cavities 10 may be readily changed by appropriate adjustment of the applied voltage. Here a diameter of about 1.2 to 1.4 nm is obtained per 1 V of anodic voltage.

Alternatively, the covering layer 6 or the non-oxidized covering layer material, like aluminium, may be applied, e.g., via a plasma deposition process on the surface 7 of the support 2 and may possibly be subsequently oxidized. This is, in particular, advantageous when only an external coating is desired; however, an extra inner coating is also possible in this way.

However, production of the covering layer 6 is not limited to the above examples, for example an oxidization of an appropriate surface layer of the support 2 may also be taken into consideration. Furthermore, the material for the covering layer 6 is not limited to aluminium oxide, but, e.g., magnesium oxide and/or titanium oxide may also be applied. Moreover, in addition to oxides, in particular, ceramic materials may also be applied for forming the covering layer 6; the mechanical properties of the resulting covering layer 6 and preferably the structure of the cavities 10 for absorbing the therapeutic agent 5 are essential.

Figure 5A:
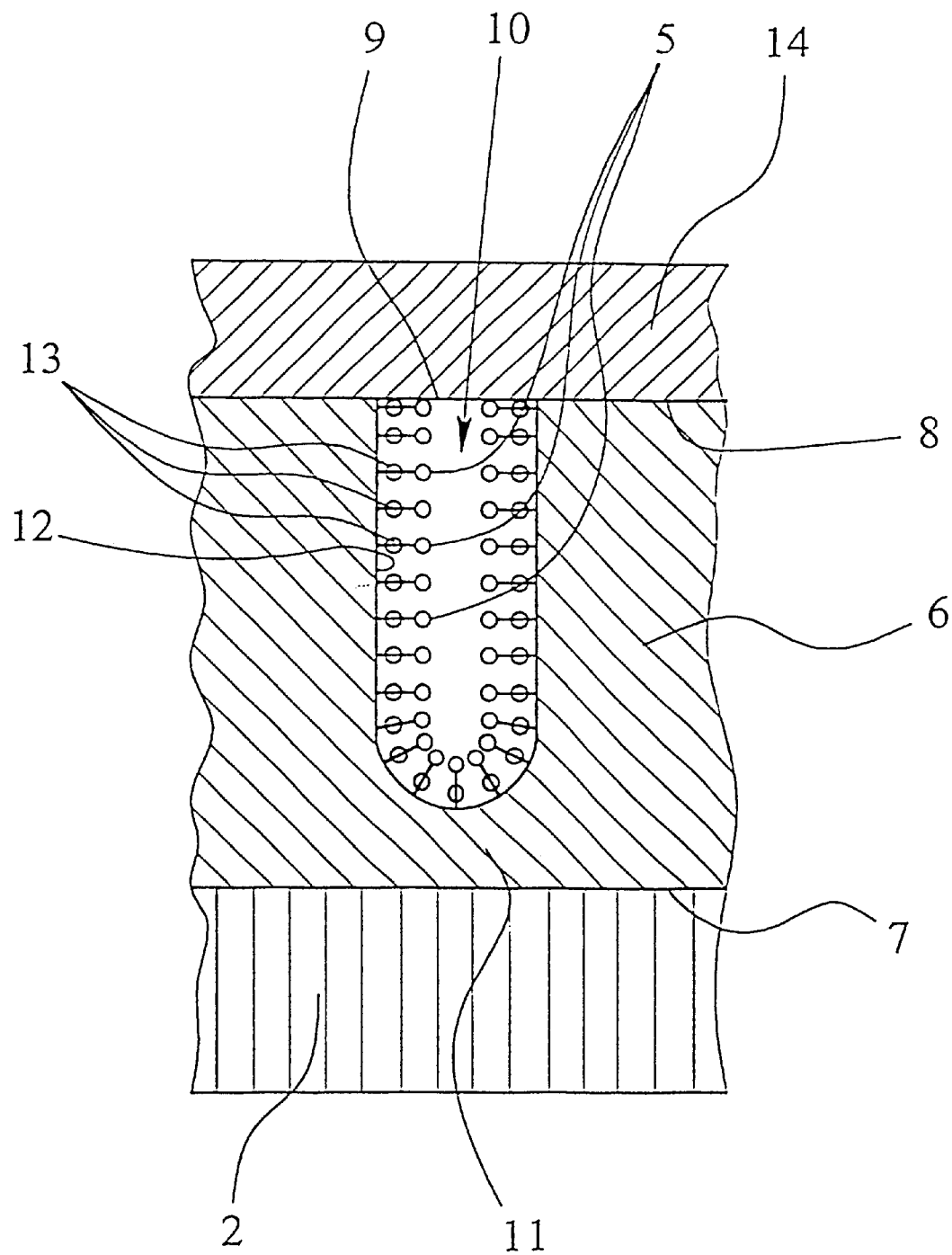
FIGS. 5a, b, c sectional enlargements of the cavities of the covering layer according to FIG. 4 and of an associated cover layer.

The schematic, enlarged sectional diagram of a cavity 10 according to FIG. 5a illustrates the possible fixing of the therapeutic agent 5 in the cavities 10 of the covering layer 6. For example, the wall 12 of the cavity 10 is provided with reaction partners such as complexing agents 13 which, for example, are bound by silanization in the cavities 10 or on their walls 12.

Instead of the exemplary complexing agents 13 in FIG. 5a, the walls 12 of the cavities 10 may also be provided with other binding partners, if needed, causing a desired binding of the therapeutic agent 5. Alternatively, at least one therapeutic agent 5 is preferably absorbed by the cavities 10 without it being bound or fixed therein. In particular, in this case, if necessary, but also normally, a cover layer 14 is preferably provided on the surface 8 of the covering layer 6 which also covers the cavities 10 and their openings 9, respectively.

In particular, the cover layer 14 is further used for preventing a premature escape or release of the therapeutic agent 5 from the cavities 10, before implantation of the implant 1. However, the cover layer 14 may also be used for preventing a direct contact between body tissue and/or fluids and the therapeutic agent 5, especially when the therapeutic agent 5 is radioactive material. As the total surface area of the openings 9 is preferably smaller, in particular substantially smaller than the surface area of the surface 8 of the covering layer 6 in contact with the cover layer 14, the cover layer 14 may adhere to the covering layer 6 very well, regardless of the therapeutic agent 5, depending on the selected material for the covering layer 6 and the cover layer 14. Preferably, the walls 12 of the cavities 10 form an essentially larger internal surface as compared with the surface 8 of the covering layer 6, in particular when fixing of the therapeutic agent in the cavities 10 is desired.

It is essential that the covering layer 6 and the optionally provided cover layer 14 be dimensioned and formed so as to safely exclude any segmentation, for example when widening the stent radially. In this respect, here, the thickness of the covering layer 6 is preferably less than 1.5 $\mu$m, preferably not more than 200 nm, and in particular from 30 nm to 150 nm. However, the thickness of the covering layer may also be up to 150 μm, in particular for absorbing larger volumes in the cavities 10.

Figure 5B:
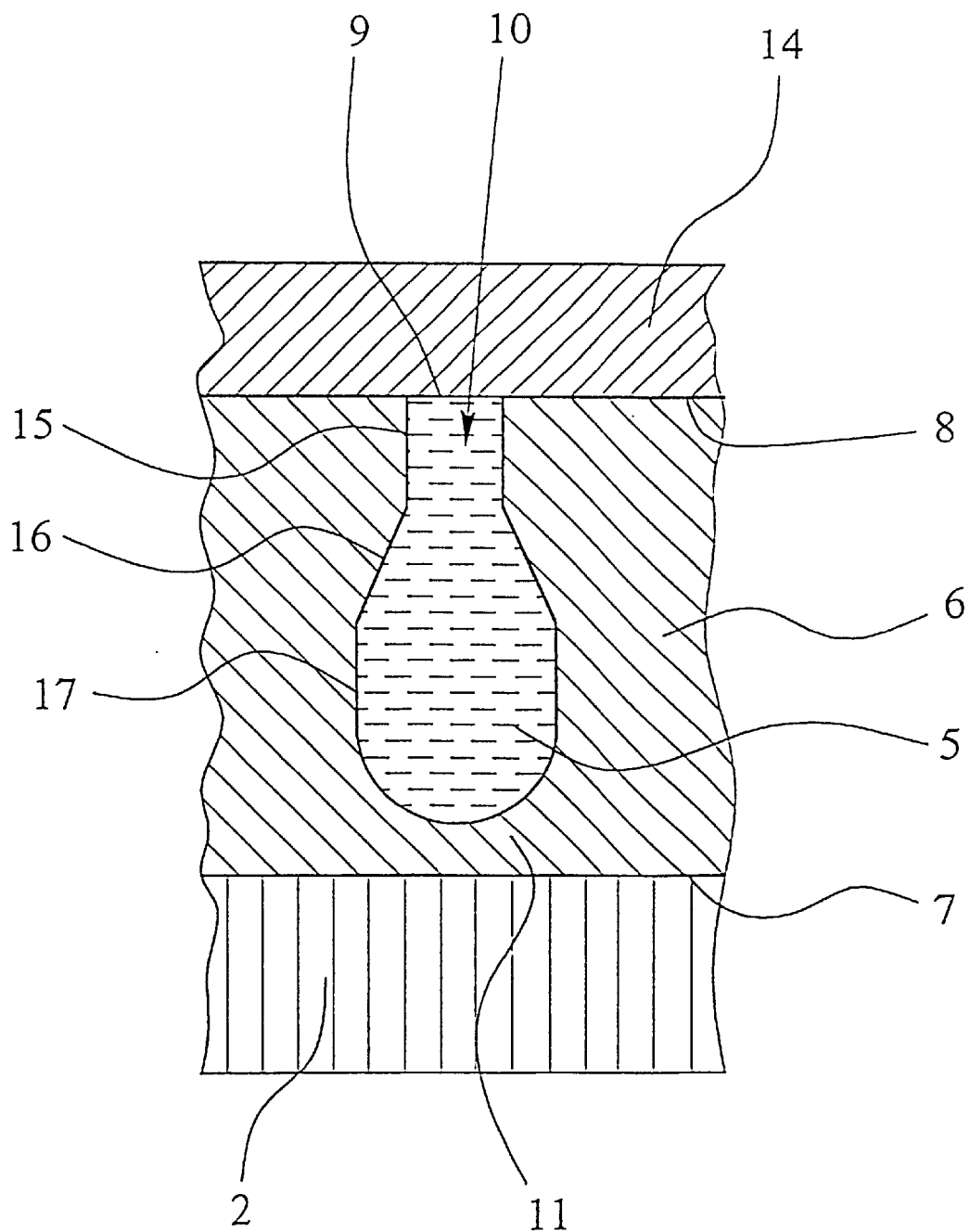

FIG. 5b shows an alternative embodiment with altered cavities 10 in a cut-out sectional view corresponding to FIG. 5a. Here, cavities 10 are approximately bottle-shaped in a section perpendicular to the main extension plane of the covering layer 6 and/or respectively comprise a reduced portion 15 in the area of the opening 9, a transition portion 16 adjacent to the portion 15 on the side opposite the opening 9 with an increasing cross-section and finally an adjacent end portion 17 with the largest cross-section or diameter. In this exemplary embodiment, the portion 15 reduced in cross-section or diameter limits the release rate or rapidity with which the therapeutic agent 5 is released from the cavities 10 in the implanted state with removed or permeable cover layer 14. Depending on the dimensioning of the cavities 10—by varying the voltage in an electrolytic anodization—it is thereby possible to achieve a desired release rate.

If necessary, the sequence of portions 15–17 of the cavities 10 illustrated as an example in FIG. 5b may also be reversed, so that portion 17 comprising the largest diameter or cross-section opens to the surface 8, so as to first achieve a very strong or high release rate and then a reduced release rate. In each case, a desired timely distribution and possibly also a spatial distribution of the liberated or released dose of therapeutic agent 5 may be set by the shape or dimensioning of the cavities 10. The definite structure of the cavities 10 is essential here.

For example, in FIG. 5b, it is indicated that a single therapeutic agent 5 is absorbed by the cavities 10. If necessary, various therapeutic agents 5, for example stacked, may also be absorbed by the cavities 10 in order to achieve successive release of the various therapeutic agents 5. Alternatively or additionally, various therapeutic agents 5 may also be absorbed, for example, in differently structured cavities 10 of the covering layer 6 and/or with different binding partners, in order to be able to achieve a possibly simultaneous release of various therapeutic agents 5 in a desired dose.

Figure 5C:
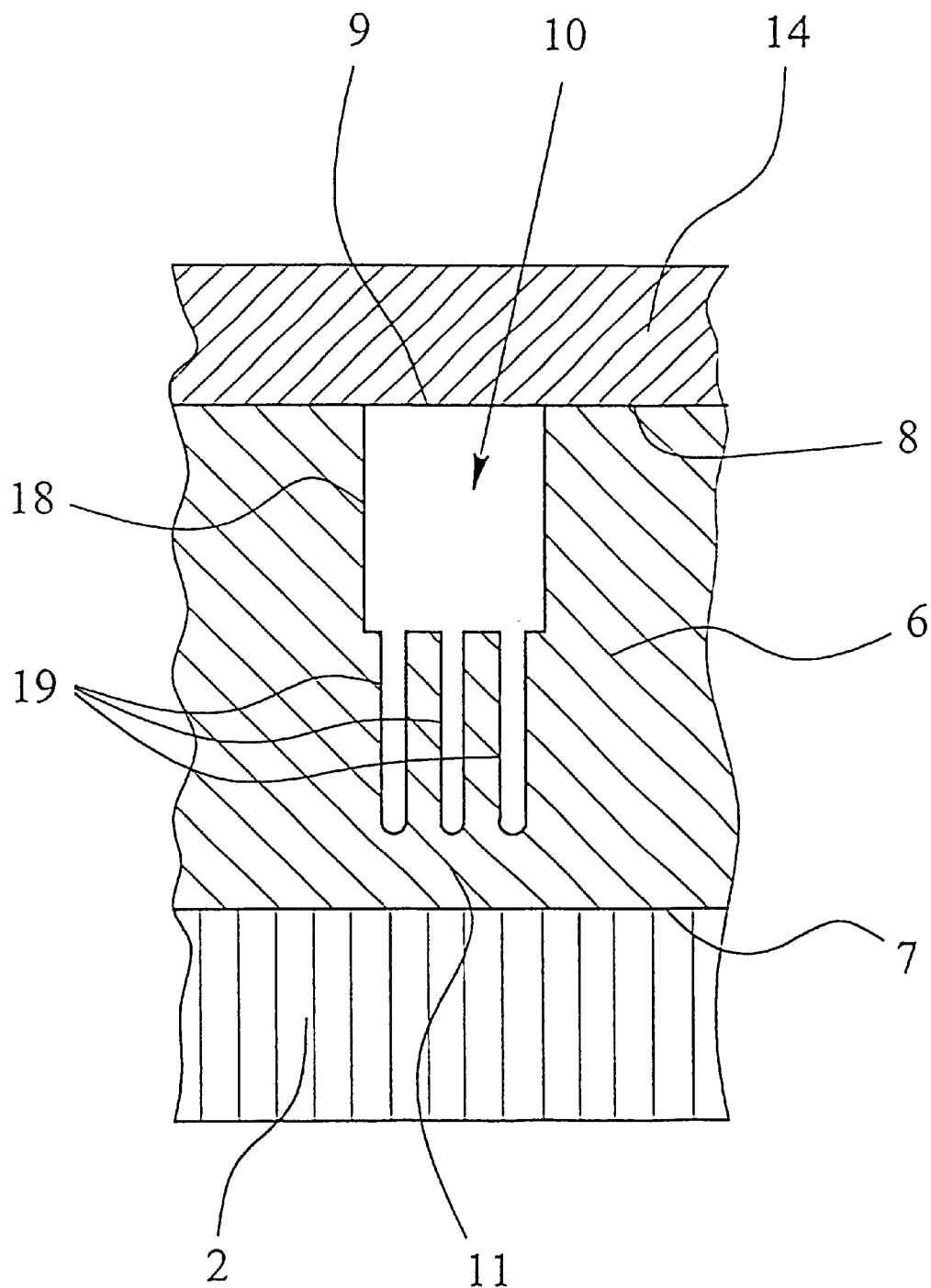

FIG. 5c, in an illustration corresponding to FIGS. 5a and 5b, shows a further exemplary embodiment of the implant 1 with altered cavities 10 once again for explaining the different implementation possibilities. In this case, the cavities 10 each comprise a first portion 18 opening to the surface 8 of the covering layer 6 and several portions 19 adjacent to the portion 18 on the end opposite the opening 9 significantly reduced in their diameter or cross-section, the root-like or projection-like portions 19 attached to portion 18 of the cavity cause a slower release or liberation of an absorbed therapeutic agent S than portion 18 when compared with the release or liberation from portion 18. If necessary, portions 18 and portions 19 of the cavities 10 may also be provided or filled with different therapeutic agents 5, wherein the length of portions 18 and 19, i.e., their perpendicular extent with respect to the main plane or surface 8 of the covering layer 6, may be adapted individually and commonly to a desired release behavior.

In order to be able to obtain a sufficiently high dose, a certain amount of the therapeutic agent(s) 5 is required which is absorbed by the cavities 10. Preferably, about $10^8$ to $10^{11}$ cavities per $cm^2$ of the surface 8 of the covering layer 6 are provided.

Figure 6:
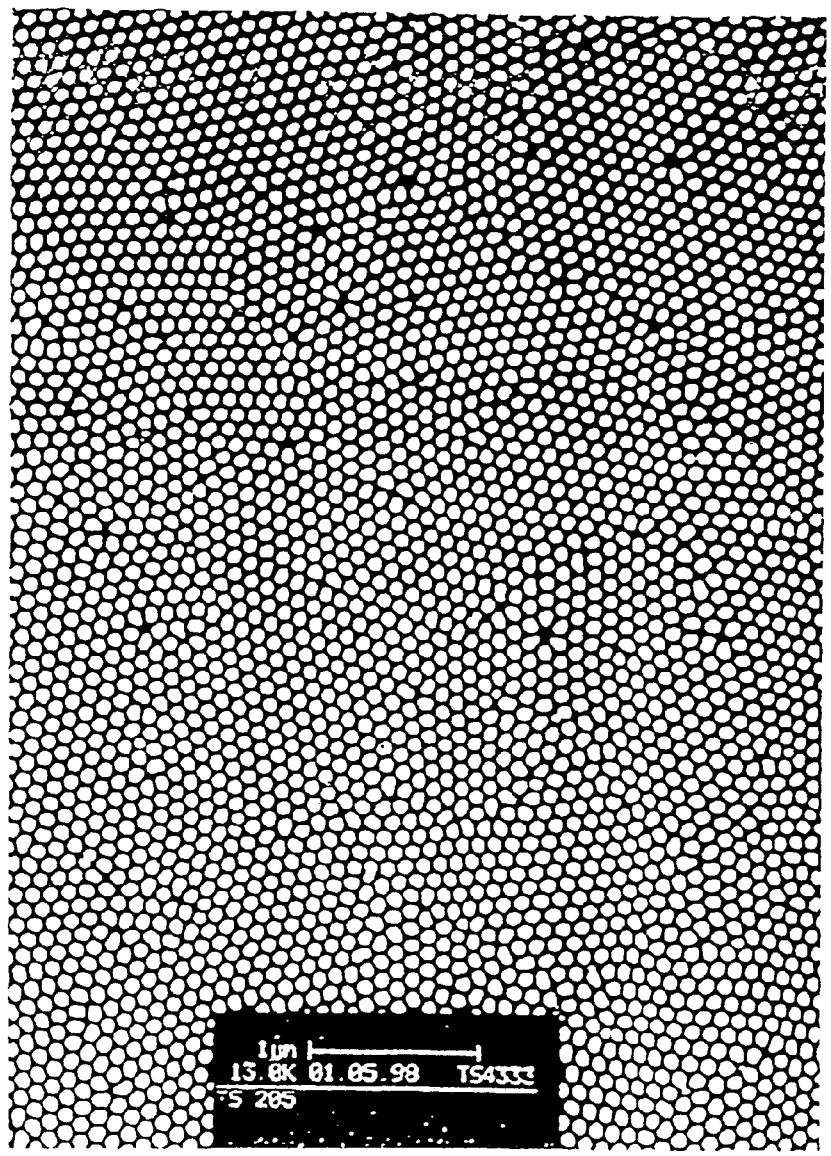
FIGS. 6, 7 electron micrographs of an aluminium oxide layer with cavities, in different enlargements.
Figure 7:
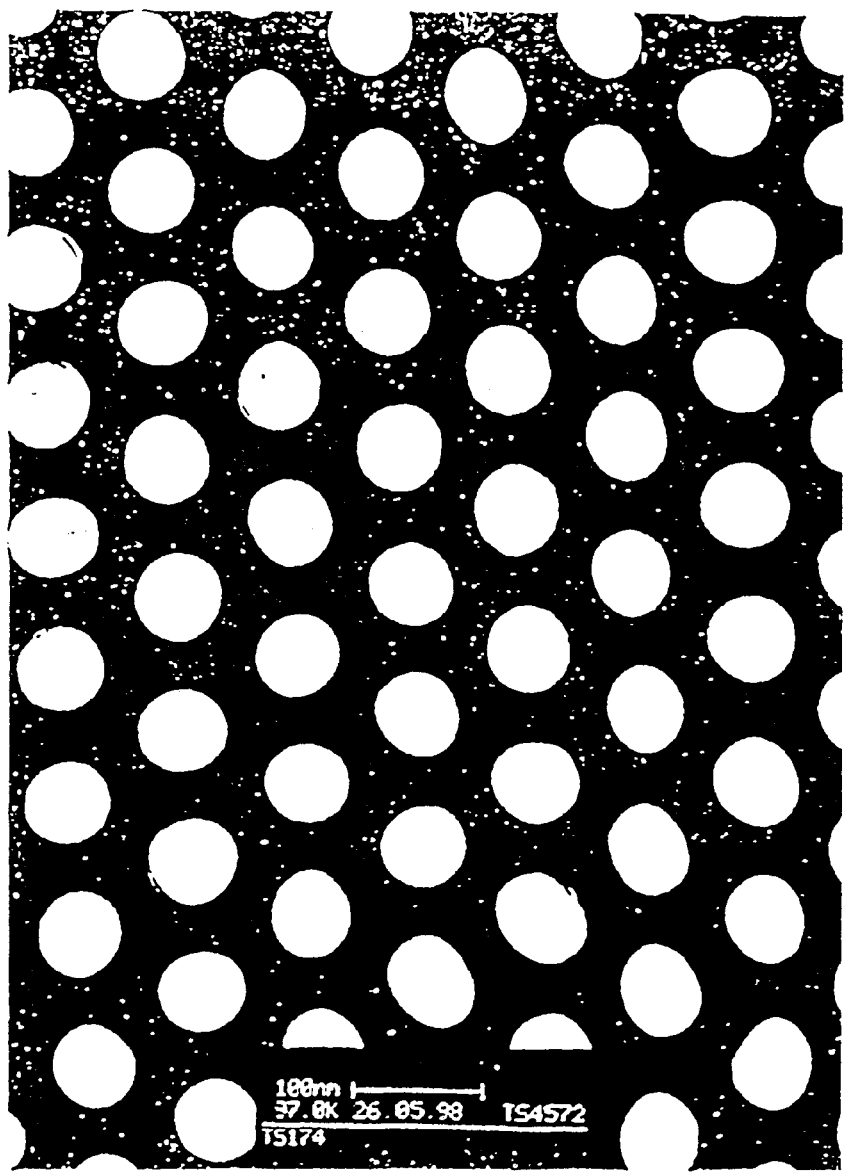

FIGS. 6 and 7 show electron micrographs of a surface of an aluminium oxide layer with different magnifications. It clearly shows how the light appearing, tube-shaped cavities are homogeneously distributed and formed in the aluminium oxide layer.

According to a more preferred exemplary embodiment, radioactive material as a therapeutic agent 5 is absorbed in the cavities 10 and in particular is fixed therein.

The schematic, enlarged sectional view of a cavity 10 according to FIG. 5a illustrates the fixing of the radioactive material in the cavities 10 of the covering layer 6. The wall 12 of the cavity 10 is provided with reaction partners or complexing agents 13, preferably thiols or carboxylates which, for example, are bound via silanization in the cavities 10 or on their walls 12, and bind or fix the radioactive material in the cavities 10 via mercapto groups, for example.

For example, the radioactive material contains radioactive technetium and/or rhenium, wherein technetium(V)- and/or rhenium(V)-compounds are in particular formed with sulphur-containing ligands which exhibit extremely high stability in vivo. According to an another example, radioactive material in the form of $^{86}Y$, $^{90}y$, $^{89}Sr$, $^{153}Sm$, $^{64}Cu$, $^{67}Cu$ and/or $^{105}Rh$ is fixed in the cavities 10 via (poly) carboxylates, wherein the carboxylates in turn are preferably bound via silanization in the cavities 10.

Preferably, the radioactive material contains various radionuclides in a desired ratio, so that an optimal dose is achieved with respect to space and/or time considerations because of the different properties of the various radionuclides. This is possible in a relatively simple way by the proposed introduction of radioactive material into the cavities 10 as, e.g., various radio-isotopes and/or various radionuclides with different half-life values, energies and/or types of radiation ($\alpha$, $\beta+$, $\beta-$, $\gamma$) may be mixed or blended in the cavities 10 and may be fixed therein, e.g., via appropriately selected complexing agents 13.

Alternatively, various radionuclides may also be introduced in succession, i.e. for example stacked, in the cavities 10 and may be fixed therein by means of appropriate or selective complexing agents 13.

Alternatively or additionally, it is possible not to completely fill up the cavities 10 with radioactive material, but to add, for example, extra filler material for stabilization and/or closure of the openings 9 when only partially filled with radioactive material 5.

The further possible different filling of the cavities 10 with radioactive material for changing the dose distribution has been already mentioned.

In particular, the diameter of the cavities 10 and/or of the openings 9 is selected so that the blood components or the molecules normally present in blood 4, which are relatively large, may not penetrate into the cavities 10 through the openings 9 because of their size. This can be ensured by forming the cavities such that the average of either the largest or average diameters of the openings 9 is from about, 5 up to a maximum of 100 nm, preferably up to a maximum of 50 nm and, more preferably, up to a maximum of 25 nm.

In order to be able to achieve a sufficiently high dose, a certain amount of radioactive material is required which is absorbed by the cavities 10. Preferably about $10^8$ to $10^{11}$ cavities 10 per $cm^2$ of the surface 8 of the covering layer 6 are provided.

Finally it should be pointed out that the proposed localization of radioactive material in the cavities 10 of a proposed covering layer 6 is not limited to implants, but it may also be applied in other components or radioactive emitters with desired radioactive properties.

What is claimed is:

1. An implant adapted for contacting body tissue and body fluids of humans or animals comprising:
a support including an at least partially formed covering layer, said covering layer having a plurality of cavities with separate openings of substantially uniform shape which are homogenously distributed on the surface of and opening to the surface of the covering layer, said cavities being adapted for absorbing at least one therapeutic agent, said covering layer consisting essentially of a metal oxide formed by electrolytic oxidation, said metal oxide being selected from the group consisting of aluminum oxide, magnesium oxide, tantalum oxide, iron oxide and tungsten oxide, said cavities being formed by the electrolytic oxidation forming said metal oxide, and said openings comprising an opening area wherein the average of either the largest or average diameters of said openings is up to 100 nm.

2. An implant, according to claim 1, wherein the support is provided with an electrolytically applied covering layer.

3. An implant, according to claim 1, wherein the support is provided with an oxidized covering layer.

4. An implant, according to claim 1, wherein the support is provided with a plasma deposition applied covering layer.

5. An implant, according to claim 1, wherein said covering layer comprises an oxidized surface of said support.

6. An implant, according to claim 1, wherein said covering layer is formed at least on outside surface portions of the support with essentially uniform thickness.

7. An implant, according to claim 1, wherein said cavities are formed longitudinally.

8. An implant, according to claim 1, wherein said cavities are formed tube-like and are each closed on at least one end.

9. An implant, according to claim 1, wherein said cavities extend essentially perpendicularly to at least one of the surface of said covering layer and the surface of said support.

10. An implant, according to claim 1, wherein said cavities each comprise sections with different dimensioned cross-sections.

11. An implant, according to claim 1, wherein said openings of said cavities are distributedly arranged over at least a portion of the surface of said covering layer with a surface density of $10^8$ to $10^{11}$/cm$^2$ over said surface.

12. An implant, according to claim 1, wherein the sum of the cross-sectional areas of the openings is at most 50% of the surface.

13. An implant, according to claim 1, wherein said openings comprise essentially the same cross-sectional opening area.

14. An implant, according to claim 1, wherein said openings have a maximum diameter of up to 50 nm.

15. An implant, according to claim 1, wherein said implant is formed as a stent.

16. An implant, according to claim 1, wherein said therapeutic agent is bound in said cavities and releasable therefrom when activated by laser or ultrasound.

17. An implant, according to claim 1, wherein said therapeutic agent is bound in said cavities and releasable therefrom by body-specific substances, body fluids, enzymes or activation substances.

18. An implant, according to claim 1, including at least one therapeutic agent in said cavities.

19. An implant, according to claim 18, wherein said therapeutic agent is chemically bound in said cavities via complexing agents.

20. An implant, according to claim 18, wherein said therapeutic agent is chemically bound in said cavities.

21. An implant, according to claim 18, wherein said therapeutic agent is bound in said cavities and releasable therefrom when a predetermined temperature is exceeded.

22. An implant, according to claim 18, comprising at least two therapeutic agents absorbed in said cavities such that said agents are releasable in succession.

23. An implant, according to claim 18, comprising at least two therapeutic agents absorbed in said cavities such that said agents are releasable at different rates.

24. An implant, according to claim 18, wherein said at least one therapeutic agent comprises radioactive material containing a predetermined amount of at least one radionuclide fixed in said cavities.

25. An implant, according to claim 24, wherein said at least radioactive material is chemically bound to a wall of said cavities.

26. An implant, according to claim 24 wherein said radioactive material is selected from the group consisting of radioactive rhenium and technetium.

27. An implant according to claim 1, wherein said covering layer and its openings are at least temporarily covered by a cover layer.

28. An implant, according to claim 27, wherein said cover layer is gold.

29. An implant, according to claim 1, wherein the thickness of said covering layer is less than 1.5 $\mu$m.

30. An implant, according to claim 1, wherein said covering layer forms a barrier layer which is impermeable to body fluids.

31. An implant, according to claim 1, wherein said covering layer covers substantially the whole surface of the support.

32. An implant, according to claim 1, wherein said cavities are formed exclusively in the covering layer.

33. An implant, according to claim 1, wherein said covering layer comprises cavities with at least one of different cross-sections, volumes and opening areas at the surface of said covering layer.

34. An implant, according to claim 1, wherein said cavities each comprise a section with branched cross-sections.

35. An implant, according to claim 1, wherein said openings have a maximum diameter of 25 nm or less.

36. An implant, according to claim 1, wherein said openings have a maximum diameter of 5 nm or greater.

37. An implant, according to claim 1, wherein said cavities and/or openings have an opening area at the surface of the covering layer which is small as compared with the diameters of the components normally found in blood.

38. A method for making an implant adapted for contacting body tissue and body fluids of humans or animals comprising a support including an at least partially formed covering layer, said covering layer having a plurality of cavities with separate openings of substantially uniform shape which are homogenously distributed on the surface of and opening to the surface of the covering layer, said cavities being adapted for absorbing at least one therapeutic agent, said covering layer consisting essentially of a metal oxide formed by electrolytic oxidation, said metal oxide being selected from the group consisting of aluminum oxide, magnesium oxide, tantalum oxide, iron oxide and tungsten oxide, said cavities being formed by the electrolytic oxidation forming said metal oxide, and said openings comprising an opening area wherein the average of either the largest or average diameters of said openings is up to 100 nm, said method comprising the steps of:

subjecting said implant to low pressure in order to evacuate the cavities;

supplying at least one of a binding agent for the therapeutic agent and the therapeutic agent to said cavities; and returning the pressure to normal.

39. A method, as claimed in claim 38, wherein said supplying is accomplished by dipping said implant into said at least one of said binding agent and said therapeutic agent, respectively.

40. A method, as claimed in claim 38, wherein at least one of said binding agent and said therapeutic agent are incorporated into said cavities by means of ultrasound.

41. A method for making an implant adapted for contacting body tissue and body fluids of humans or animals comprising a support including an at least partially formed covering layer, said covering layer having a plurality of cavities with separate openings open to a surface of the covering layer, said cavities being adapted for absorbing at least one therapeutic agent, said covering layer consisting essentially of an electrolytically oxidized metal oxide selected from the group consisting of aluminum oxide, magnesium oxide, tantalum oxide, iron oxide and tungsten oxide, and said openings comprising an opening area wherein the average of either the largest or average diameters of said openings is up to 100 nm, said method comprising the steps of:

provinding said cavities with at least one of complexing agents and reaction partners for chemically binding the therapeutic agent therein and, thereafter, introducing said therapeutic agent into said cavities.

42. A method, as claimed in claim 41, wherein said therapeutic agent is incorporated in said cavities by subjecting said implant to low pressure.

43. A method of treating humans or animals with a therapeutic agent comprising:

contacting body tissue or body fluids of said treated human or animal with an implant containing said therapeutic agent, said implant comprising a support including an at least partially formed covering layer, said covering layer having a plurality of cavities with separate openings of substantially uniform shape which are homogenously distributed on the surface of and opening to the surface of the covering layer, said cavities being adapted for absorbing at least one therapeutic agent, at least one therapeutic agent in said cavities, said covering layer consisting essentially of a metal oxide formed by electrolytic oxidation, said metal oxide being selected from the group consisting of aluminum oxide, magnesium oxide, tantalum oxide, iron oxide and tungsten oxide, said cavities being formed by the electrolytic oxidation forming said metal oxide, and said openings comprising an opening area wherein the average of either the largest or average diameters of said openings is up to 100 nm.

44. A method for making an implant adapted for contacting body tissue and body fluids of humans or animals comprising a support including an at least partially formed covering layer, said covering layer having a plurality of cavities with separate openings open to a surface of the covering layer, said cavities being adapted for absorbing at least one therapeutic agent, said covering layer consisting essentially of an electrolytically oxidized metal oxide selected from the group consisting of aluminum oxide, magnesium oxide, tantalum oxide, iron oxide and tungsten oxide, and said openings comprising an opening area wherein the average of either the largest or average diameters of said openings is up to 100 nm, said method comprising the step of:

incorporating at least one of a binding agent for a therapeutic agent and a therapeutic agent into said cavities by means of ultrasound.

45. An implant adapted for contacting body tissue and body fluids of humans or animals comprising:

a support including an at least partially formed covering layer, said covering layer having a plurality of cavities with separate openings open to a surface of the covering layer, said cavities being adapted for absorbing at least one therapeutic agent, said covering layer consisting essentially of a metal oxide formed by electrolytic oxidation, said metal oxide being selected from the group consisting of aluminum oxide, magnesium oxide, tantalum oxide, iron oxide and tungsten oxide, said cavities being formed similarly-shaped by the electrolytic oxidation forming said metal oxide, and said openings comprising an opening area wherein the average of either the largest or average diameters of said openings is up to 100 nm, including at least one therapeutic agent in said cavities, wherein said at least one therapeutic agent comprises radioactive material containing a predetermined amount of at least one radionuclide fixed in said cavities, and wherein said radioactive material is chemically bound in said cavities via sulphur groups.

46. An implant adapted for contacting body tissue and body fluids of humans or animals comprising:

a support including an at least partially formed covering layer, said covering layer having a plurality of cavities with separate openings open to a surface of the covering layer, said cavities being adapted for absorbing at least one therapeutic agent, said covering layer consisting essentially of a metal oxide formed by electrolytic oxidation, said metal oxide being selected from the group consisting of aluminum oxide, magnesium oxide, tantalum oxide, iron oxide and tungsten oxide, said cavities being formed similarly-shaped by the electrolytic oxidation forming said metal oxide, and said openings comprising an opening area wherein the average of either the largest or average diameters of said openings is up to 100 nm; and at least one therapeutic agent in said cavities, wherein said therapeutic agent is bound in said cavities and releasable therefrom when a predetermined temperature is exceeded.

47. A method for making an implant adapted for contacting body tissue and body fluids of humans or animals comprising a support including an at least partially formed covering layer, said covering layer having a plurality of cavities with separate openings open to a surface of the covering layer, said cavities being adapted for absorbing at least one therapeutic agent, said covering layer consisting essentially of a metal oxide formed by electrolytic oxidation, said metal oxide being selected from the group consisting of aluminum oxide, magnesium oxide, tantalum oxide, iron oxide and tungsten oxide, said cavities being formed similarly-shaped by the electrolytic oxidation forming said metal oxide, and said openings comprising an opening area wherein the average of either the largest or average diameters of said openings is up to 100 nm, said method comprising the steps of:

subjecting said implant to low pressure in order to evacuate the cavities;

supplying at least one of a binding agent for the therapeutic agent and the therapeutic agent to said cavities; and returning the pressure to normal, wherein at least one of said binding agent and said therapeutic agent are incorporated into said cavities by means of ultrasound.

48. An implant adapted for contacting body tissue and body fluids of humans or animals comprising:

a support including an at least partially formed covering layer, said covering layer having a plurality of cavities with separate openings open to a surface of the covering layer, said cavities being adapted for absorbing at least one therapeutic agent, said covering layer consisting essentially of a metal oxide formed by electrolytic oxidation, said metal oxide being selected from the group consisting of aluminum oxide, magnesium oxide, tantalum oxide, iron oxide and tungsten oxide, said cavities being formed similarly-shaped by the electrolytic oxidation forming said metal oxide, and said openings comprising an opening area wherein the average of either the largest or average diameters of said openings is up to 100 nm, wherein said therapeutic agent is bound in said cavities and releasable therefrom when activated by laser or ultrasound.

* * * * *